United States Patent [19]

Tunis

[11] Patent Number: 5,549,614
[45] Date of Patent: Aug. 27, 1996

[54] APPARATUS FOR FOLDING FLEXIBLE INTRAOCULAR LENSES

[76] Inventor: Scott W. Tunis, 2000 NE 49th St., Ft. Lauderdale, Fla. 3308

[21] Appl. No.: 364,013

[22] Filed: Dec. 27, 1994

Related U.S. Application Data

[63] Continuation of Ser. No. 48,328, Mar. 18, 1993, abandoned.

[51] Int. Cl.⁶ .................................................. A61F 9/00
[52] U.S. Cl. ............................................. 606/107; 623/6
[58] Field of Search ........................ 623/4, 6; 606/107, 606/1

[56] References Cited

U.S. PATENT DOCUMENTS

| | | | |
|---|---|---|---|
| 4,269,307 | 5/1981 | LaMaye | 623/6 |
| 4,573,998 | 3/1986 | Mazzocco . | |
| 4,605,409 | 8/1986 | Kelman . | |
| 4,664,667 | 5/1987 | Kelman . | |
| 4,681,102 | 7/1987 | Bartell . | |
| 4,684,014 | 8/1987 | Davenport | 623/6 |
| 4,697,697 | 10/1987 | Graham et al. | 623/6 |
| 4,702,244 | 10/1987 | Mazzocco . | |
| 4,715,373 | 12/1987 | Mazzocco et al. . | |
| 4,785,810 | 11/1988 | Baccala et al. . | |
| 4,834,750 | 5/1989 | Gupta . | |
| 4,844,065 | 7/1989 | Faulkner . | |
| 5,100,410 | 3/1992 | Dulebohn | 606/107 |
| 5,171,241 | 12/1992 | Buboltz et al. . | |
| 5,171,319 | 12/1992 | Keates et al. . | |
| 5,176,686 | 1/1993 | Poley . | |
| 5,178,622 | 1/1993 | Lehner, II . | |
| 5,190,553 | 3/1993 | Kanert et al. | 606/107 |
| 5,281,227 | 1/1994 | Sussman | 606/107 |
| 5,290,293 | 3/1994 | Van Noy et al. | 606/107 |

*Primary Examiner*—Gary Jackson
*Assistant Examiner*—Glenn Dawson
*Attorney, Agent, or Firm*—Millen, White, Zelano, & Branigan, P.C.

[57] ABSTRACT

Apparatus for and methods of preparing and inserting flexible intraocular lenses, through incisions in ocular tissue made during phacoemulsification cataract surgery. The incisions are preferably no longer than 3 mm. The intraocular lens is placed on a template which facilitates multiple folding of the intraocular lens. Multiple folds in the lens are then accomplished with the template providing necessary and proper orientation, stabilization, and positioning of the lens. The intraocular lens folded using the template is held with a lens-insertion forceps and is inserted and released inside the eye, whereupon the lens unfolds in its proper position and configuration inside the eye. An intraocular lens having both plate haptics and J-style or C-style haptics is provided.

6 Claims, 6 Drawing Sheets

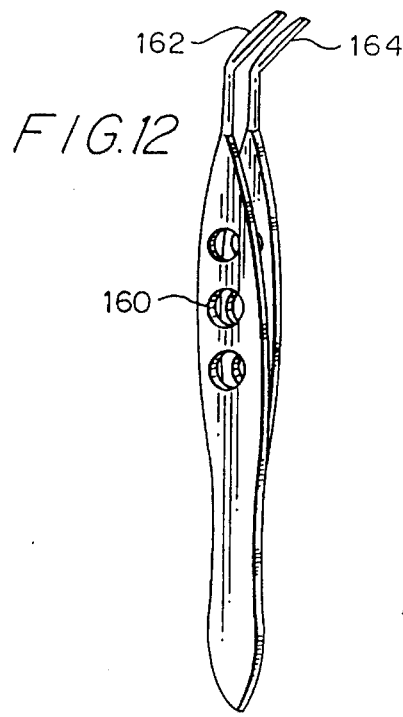
FIG.12
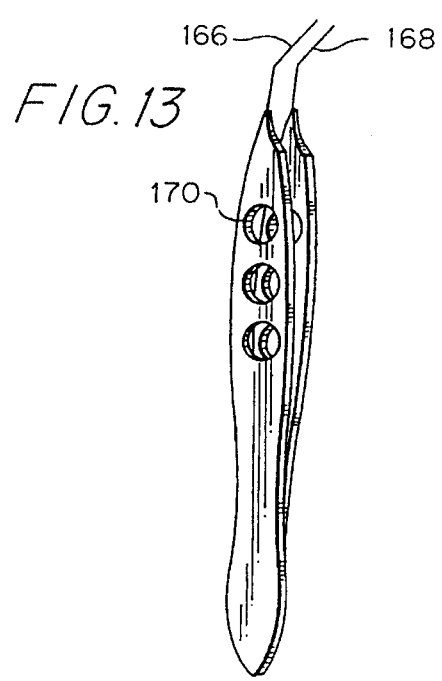
FIG.13
FIG.14
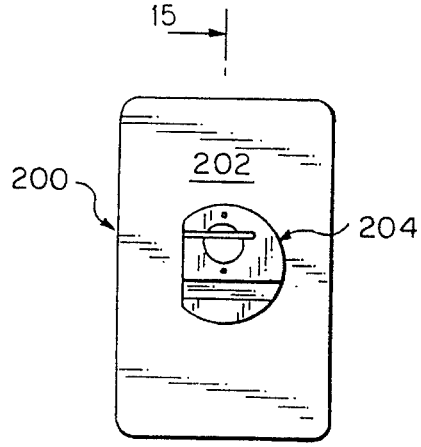
FIG.15
FIG.16
FIG.17
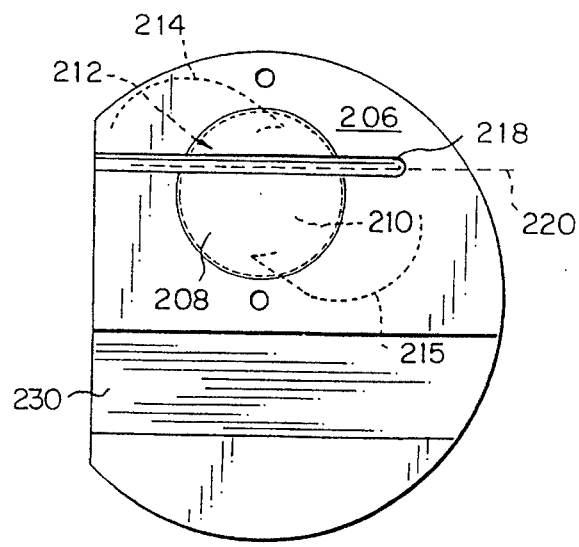

APPARATUS FOR FOLDING FLEXIBLE INTRAOCULAR LENSES

This application is a continuation, of application Ser. No. 08/048,328, filed Mar. 18, 1993 now abandoned.

BACKGROUND OF THE INVENTION

1. Field of the Invention

The present invention relates to the methods of and apparatus for preparing and inserting flexible intraocular lenses used in the field of ophthalmology wherein flexible intraocular lenses made of silicone and/or other deformable materials are inserted into the eye to replace natural lenses during cataract surgery, and to a configuration for flexible intraocular lenses. More particularly, the invention relates to methods, apparatus and lenses used in the field of ophthalmology wherein flexible intraocular lenses made of silicone and/or other deformable materials are inserted into the eye to replace the natural lens during cataract surgery.

2. Background Art

In cataract surgery, a cataractous human lens is removed through a 3 mm or larger incision by phacoemulsification. A prosthetic intraocular lens is then substituted for the human lens. The intraocular lens obviates the patient's need for a high dioptric power spectacle correction after surgery, which would otherwise be necessary.

Intraocular lenses may be made of flexible materials such as silicone. Although lenses made of these materials have dimensions in their uncompressed state which are larger than 3 mm, such lenses may be folded in various configurations and inserted through 3 mm or slightly larger incisions. When using flexible intraocular lenses, surgical incisions necessary for performing cataract surgery need not be enlarged following phacoemulsification. Accordingly, surgically induced trauma is minimized, healing and convalescence time are reduced, visual recovery for the patient is expedited, and the chance of intraoperative and postoperative complications relative to the wound are minimized.

Flexible intraocular lenses have two essential components, the first being a central optic component which is round or oval in shape and approximately between five and seven millimeters in diameter. The optic component replaces the dioptric power of the cataractous lens after cataract extraction. The second component(s) are attached to the optic component, and extend peripherally therefrom. Known as haptics, these provide internal fixation and centration of the intraocular lens after its insertion into the eye. The haptics may be flexible plates extending outward from the optic component as a unitary extension thereof. Alternatively, the haptics may be joined to the optic component and configured as open loops, termed "C" or "J" loops. The function of both haptic structures is similar.

The patent literature includes a number of patents directed to methods, apparatus and lenses utilized in phacoemulsification cataract surgery. Of particular interest in U.S. Pat. No. 4,681,102 to Bartell incorporated herein by reference which is directed to apparatus for and methods of inserting flexible intraocular lenses through 3 mm incisions. While Bartell suggests an approach to the general technique, there is a need for simpler alternative approaches which are easy to perform and employ ordinary ophthalmological surgical instruments. In addition, there is a need for approaches which allow insertion of flexible intraocular lenses through smaller incisions less than 3 mm in length, and for methods and apparatus applicable to further reducing the effective size of the intraocular lens prior to its insertion. This need is made evident by a host of U.S. Pat. Nos. such as 5,178,622; 5,171,319; 5,171,241; 5,176,686; 4,950,289; 4,894,062; 4,836,202; 4,834,751; 4,664,667; 4,715,373; 4,763,650; 4,785,810; 4,834,750; 4,844,065; and 4,862,885, each of which is incorporated herein by reference.

SUMMARY OF THE INVENTION

It is an object of the instant invention to provide new and improved methods of and apparatus for preparing and inserting flexible intraocular lenses.

Upon further study of the specification and appended claims, further objects and advantages of this invention will become apparent to those skilled in the art.

Broadly, the invention contemplates methods of folding intraocular lenses utilizing first and second forceps in combination with a template, wherein the template receives the first forceps with first blades closing in one direction and receives the second forceps with second blades angularly oriented to close substantially normal to the first blades; the template facilitating positioning the first blades between the second blades, whereby the blades cooperate to fold the lens for insertion through a surgical incision of minimal length in the eye.

In a more specific first embodiment, the invention contemplates methods of folding flexible intraocular lenses with plate haptics comprising the steps of:

(a) positioning the flexible intraocular lens in a relaxed state on an anvil having a first surface engaging the haptic plates of the lens;

(b) deforming the haptic plates by pressing the lens towards a second surface on the anvil, the second surface having a diameter less than that of the first surface to deflect the haptic plates so as to extend transverse to the optical portion;

(c) folding both of the haptic plates to overlie the optical portion;

(d) while holding the haptic plates in an overlying relationship with respect to the optical portion, folding the optical portion in half between the haptic plates to configure the folded intraocular lens in a W-shape; and (e) squeezing the lens while in a W-shape to decrease the lateral dimension thereof, whereby the lens may be inserted through a surgical incision of minimal length.

In a more specific second embodiment, the invention contemplates methods of folding flexible intraocular lenses with loop-style haptics comprising the steps of:

(a) positioning the lens in a relaxed state on a holding portion of a template having a groove therebeneath;

(b) gripping the lens with a first holding forceps by sliding one blade of the first holding forceps through the groove under the lens and squeezing the first holding forceps;

(c) placing the lens between the blades of a second folding forceps while gripping the lens with the first holding forceps by urging one side of the lens against one blade of the second folding forceps to fold the lens into an S-shape;

(d) disengaging the blades of the holding first forceps from the lens; and (e) squeezing the blades of the first folding forceps to decrease the lateral dimension thereof, whereby the lens may be inserted through a surgical incision of minimal length.

The methods of the instant invention further comprise a surgical procedure wherein a lens folded into a W-shape or an S-shape utilizing the aforedescribed methods and structures having a transverse dimension of less than 3 mm is inserted by forceps through an incision in the eye for subsequent expansion within the eye, so that the lens is centered within the visual axis, and supported by the posterior capsule.

In order to facilitate the first methods, the instant invention further contemplates a first apparatus wherein a flexible intraocular lens with plate haptics is folded on an anvil having first and second platforms therein with a recess underlying the second platform. The apparatus is utilized to initially mount the lens thereon, while an instrumentality, such as the blades of a forceps, are used to press the lens from the first platform to the second platform and to fold the plate haptics over the optical portion of the lens. The apparatus further facilitates using an instrumentality such as the blades of a second forceps to fold the optical portion in half, whereby one side of the optical portion has the plate haptics in overlying relationship therewith and the other side of the optical portion is engaged by a blade to move the entire folded lens between the first blades, whereby the first tines hold the lens folded in a W-shape.

In order to facilitate the second method, a template is provided having a circular recess thereon for receiving the lens. The circular recess has a groove therebeneath for receiving one blade of the holding forceps. Disposed adjacent to the circular recess is a second groove for receiving the blades of the second forceps whereby the lens is deformed into an S-shape by pressing one edge of the lens against one blade of the second forceps while turning the blades of the first forceps. The second groove is of a width sufficient to allow the blades of the second forceps to receive the initially deformed lens therebetween for subsequent squeezing by the second forceps.

Finally, the invention contemplates a flexible intraocular lens having an optical portion and a pair of haptic flanges extending laterally therefrom, as well as a pair of resilient loop style haptics extending therefrom. The resilient loop style haptics extend in a direction generally normal to the haptic flanges from one surface of the optical portion at an angle with respect to the general plane of the lens.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

FIG. 12 is a perspective view of lens-folding forceps used to practice the method of the instant invention;

FIG. 13 is a perspective view of lens-holding forceps used to practice the method of the instant invention;

FIG. 14 is an actual size top view of a second embodiment of a template used to practice a second method according to the instant invention;

FIG. 15 is a side view of the template of FIG. 14;

FIG. 16 is a cross-section taken on lines 16—16 of FIG. 14;

FIG. 17 is an enlarged top view of an anvil portion of the template of FIGS. 14–15;

DETAILED DESCRIPTION

The present invention provides methods of and apparatus for preparing and inserting flexible intraocular lenses and at least one configuration for flexible intraocular lenses which may be utilized with the apparatus to practice the method. In accordance with the method, apparatus and flexible intraocular lens, the lens may be folded to a diameter of less than 50% of its original diameter and inserted into a small incision, preferably less than 3 mm, made in the ocular tissue of a human eye. Since the flexible intraocular lens is of a resilient material possessing memory characteristics, the lens then expands to its original diameter so as to properly center within the eye.

FIGS. 1–5: The Procedure in General

Figure 1:
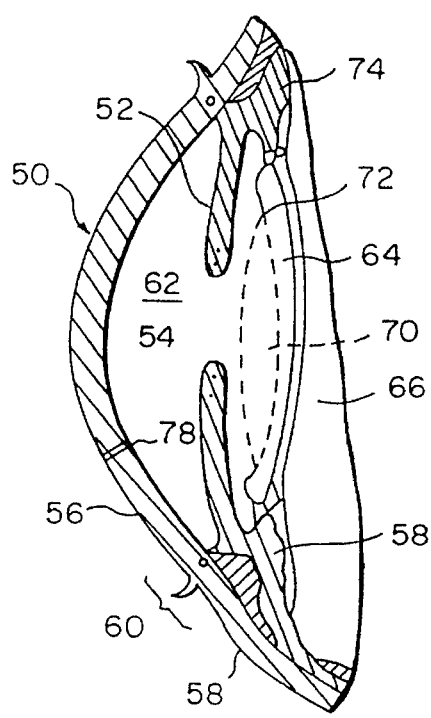
FIG. 1 is an enlarged, partial side sectional view of the anterior portion of a human eye, illustrating the internal condition of the ocular area during phacoemulsification cataract surgery.

Referring now to the drawings, FIG. 1 represents a side cross-sectional view of an anterior portion of an eye, designated generally by the numeral 50, illustrating the major ocular components thereof. The eye 50 includes an iris 52 which dilates to provide the opening of adjustable diameter which defines the pupil 54. The cornea 56 which is composed of clear tissue is attached to the sclera 58 at the limbus 60. The illustrated anterior segment 50 of the eye is divided into two principle chambers at the iris 52 and pupil 54, wherein an anterior chamber 62 is defined by the space between the cornea 56 and the iris 52 and a posterior chamber 64 is defined by the space between the iris 52 and the vitreous 66. Shown in dotted lines and disposed in the posterior chamber 64, is a hard, clear, crystalline lens 70 which is attached by zonular fibers 72 to the ciliary body 74.

Due to age or disease, the crystalline lens 70 can become cataractous preventing the lens from transmitting images therethrough to the retina (not shown) of the eye 50 and thus impairing or destroying sight. Over the years, various surgical procedures have been developed for removing the crystalline lens 70 after it has been compromised by a cataract. A preferable procedure is phacoemulsification wherein the lens is emulsified and removed by aspiration. This is done through a small incision 78 (see FIG. 1) through the limbus 60 wherein a microsurgical instrument is inserted through the anterior chamber 62 and into the posterior chamber 64. Preferably, the incision 78 is as small as possible, for example, less than 3 mm.

Figure 2:
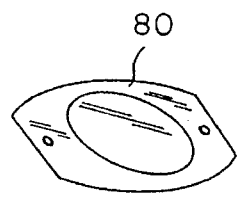
FIG. 2 is an enlarged view of a first flexible intraocular lens with plate haptics for insertion in the eye of FIG. 1.
Figure 3:
FIG. 3 is an enlarged view of a second flexible intraocular lens with loop-style haptics for insertion into the eye of FIG. 1.
Figure 4:
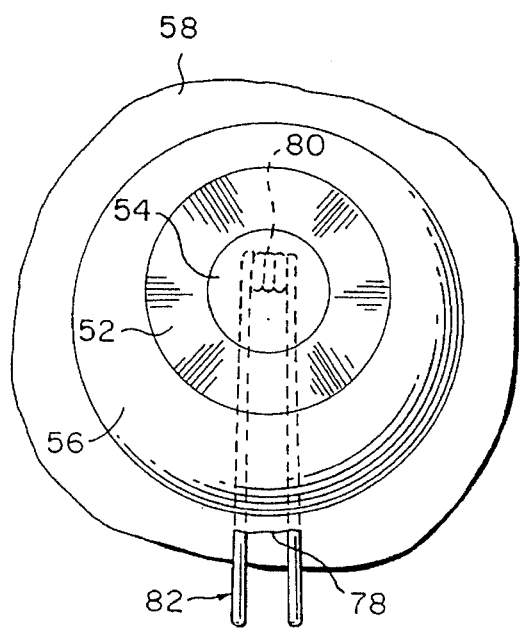
FIG. 4 is a front view of an eye having the intraocular lens of either FIG. 2 or FIG. 3 being inserted therein while the lens is in a folded configuration.
Figure 5:
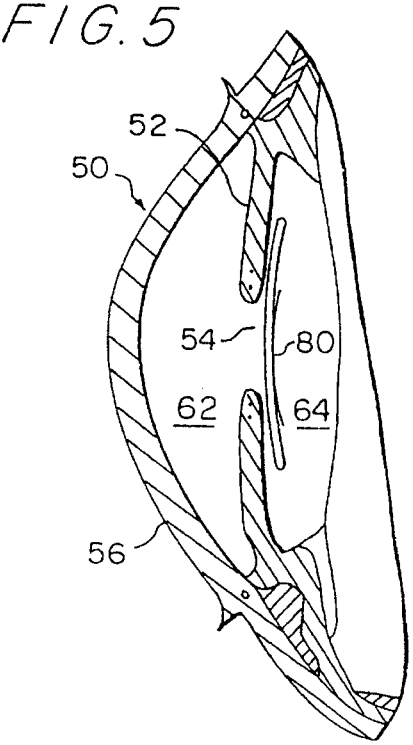
FIG. 5 is a sectional view of a portion of the eye of FIG. 1 showing the lens, such as the lens of FIG. 2, expanded and positioned in the posterior chamber behind the iris of the eye after the cataractous lens has been removed therefrom.
Figure 6:
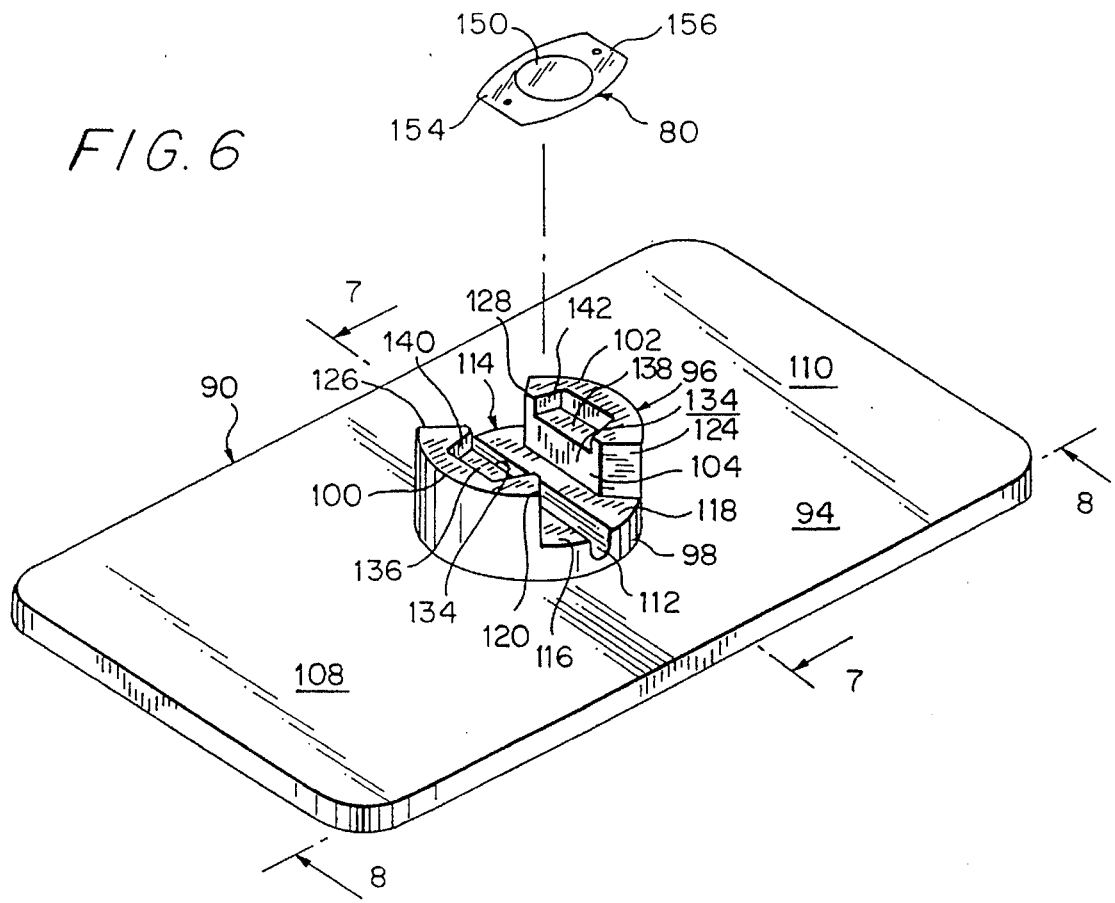
FIG. 6 is an enlarged perspective view of a first embodiment of a template configured in accordance with the instant invention for practicing a first method of the instant invention.

Referring now to FIGS. 2–4, the length of the incision 78 is in part determined by the size of the replacement lens which, in accordance with the principles of one embodiment of the instant invention, is a intraocular such as lens 80 (FIG. 2) or lens 81 (FIG. 3) which is foldable to a dimension small enough to slide through the incision 78. The lenses 80 and 81 shown in FIGS. 2 and 3 are in their expanded mode and in FIG. 4 in a folded mode. When one lens 80 or 81 is in its folded mold, it is inserted by forceps 160 (see FIG. 12) through the incision 78. After the lens 80 or 81 has been inserted, it is released by the forceps 82 and expands within the posterior chamber 64 as is seen in FIG. 5. In FIG. 5, the lens 80 is unfolded in the posterior chamber 64 to overlie the back of the iris 52 and cover the pupil 54. The lens 80 functions in a fashion substantially identical to the natural crystalline lens 70 (FIG. 1, dotted lines) now removed by phacoemulsification.

FIGS. 6–10: First Embodiment of the Template

Referring now to FIGS. 6–10, there is shown a template, designated generally by the numeral 90, configured to provide a first embodiment of an apparatus in accordance with the principles of the instant invention for folding the lens 80 so that the lens may be inserted through the incision 78 (FIG. 4) with forceps, such as the forceps 82, prior to expanding to the unfolded or unstressed configuration of FIG. 5. The illustrated template 90 is substantially enlarged in FIGS. 6, 9 and 10 for clarity and in actual size is approximately the size illustrated in FIGS. 7 and 8. The template of FIGS. 6–10 is configured to fit any of the currently available flexible intraocular lenses having plate haptics.

The template 90 includes a template base 94 upon which is mounted an anvil 96. The anvil 96 comprises a circular anvil base 98 fixed to the template base 94 and a pair of shoulders 100, 102, which project upwardly from the anvil base to define a slot 104 therebetween. The slot 104 is oriented in alignment with the minor axis 106 of the template base 94. A pair of wings 108 and 110 are provided by the template base 94 for holding the template 90 in place by clamps, or the like, with minimal interference with access to the slot 104.

Figure 7:
FIG. 7 is an actual size, sectional view taken along lines 7—7 of FIG. 6.
Figure 8:
FIG. 8 is an actual size side view of FIG. 6 viewed from the direction of cross-section 7.
Figure 9:
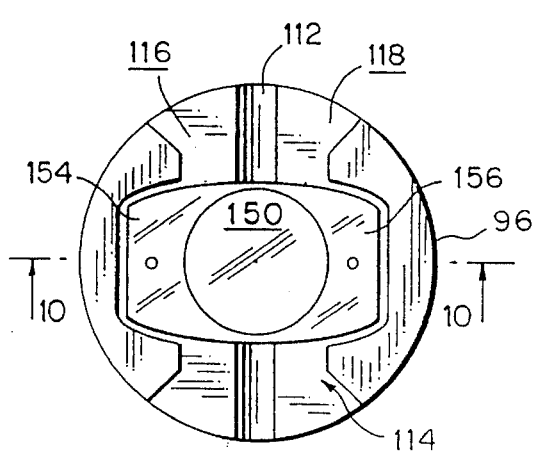
FIG. 9 is an enlarged, top view of an anvil portion of the template of FIG. 6.
Figure 10:
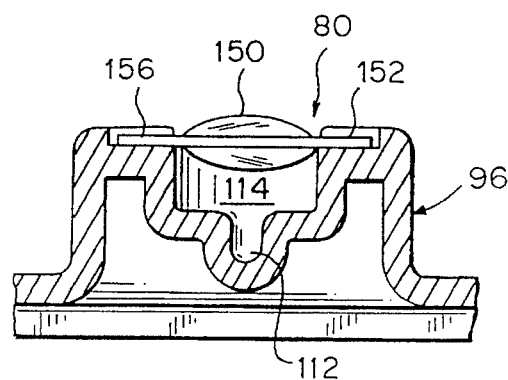
FIG. 10 is a sectional view taken along lines 10—10 of FIG. 9.

The anvil base 98 includes an instrument groove 112 aligned with the axis 106 and the slot 102 for receiving a blade of a forceps (such as the forceps shown in FIG. 13), as will be further explained hereinafter. Just above the instrument groove 112 is platform or land 114 which is defined by a pair of stationary lands 116 and 118 bordered by the shoulders 100 and 102. The shoulders 100 and 102 are mirror images of one another and each have pairs of opposed bevelled ends 120, 124 and 126, 128, as well as a pair of parallel walls 132 and 134 disposed above and set laterally of the optic platform 114 are a pair of stationary haptic platforms halves 136 and 138 separated by the slot 104. In the embodiment of FIGS. 7 and 8, the haptic platforms 136 and 138 are indentations defined by walls 140 and 142 which generally conform the shape of the plate haptics of the lens 80. Since the stationary platform halves 136 and 138 extend normal to the axis of orientation 106, the platform halves orient the lens 80 for subsequent folding. The widths of the haptic platforms 136 and 138 are less than the lengths of the vertical walls 132 and 134 measured in the direction of the instrument groove 112.

The lens 80 is defined by an optical portion 150 and plate haptics 154, 156. The optic and haptic portions of the flexible intraocular lens 80 cooperates with the structure of the anvil 96 when folding the lens 80.

FIGS. 11A–11J, 12 and 13: Practicing the Method of the Instant Invention Using the Apparatus of the Instant Invention Referring now to FIGS. 11a–11i, 12 and 13, it is shown how the apparatus of the instant invention allows a surgeon to practice the method of the instant invention, wherein a first folding forceps 160 having blades 162 and 164 cooperate with the general groove 104 and with the blades 166 and 168 of a second holding forceps 170 to fold a flexible intraocular lens such as the lens 80 of FIG. 2.

Figure 11A:
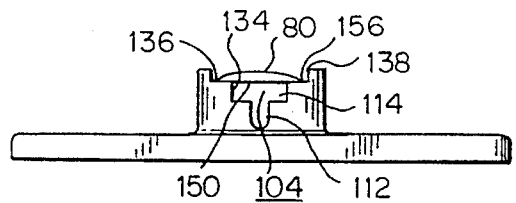
FIGS. 11a–11i are side views of the template shown in FIGS. 6–10, diagrammatically illustrating a first method of folding a lens with plate haptics, such as the lens of FIG. 2, in accordance with the principles of the instant invention.

As is seen in FIG. 11a, the flexible lens 80 is inserted into the groove 104 so that the haptics 154 and 156 rest on the haptic platforms 136 and 138 which provide a first surface, with the optic portion 150 suspended over the optic platform 114 which provides a second surface and the instrument groove 112.

Figure 11B:
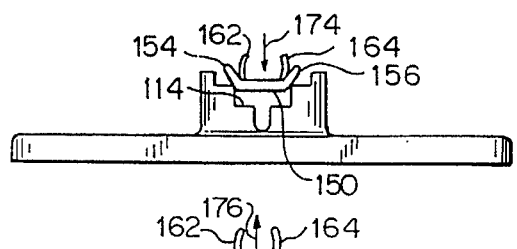

As is seen in FIG. 11b, the blades 162 and 164 of the first folding forceps 160 (FIG. 12) are then used to push the lens 80 in the direction of arrow 174 toward the optic platform or land 114. This causes the haptic portions 154 and 156 of the lens 80 to deflect upwardly as the optical portion 150 approaches the platform 114. The vertical walls 132 and 134 serve to help bend the plate haptics 154 and 156 as is seen in FIG. 11b and then serve to retain the plate haptics bent substantially normal to the lens portion 150 as seen in FIG. 11C.

Figure 11C:
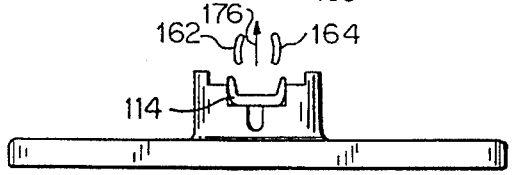
Figure 11D:
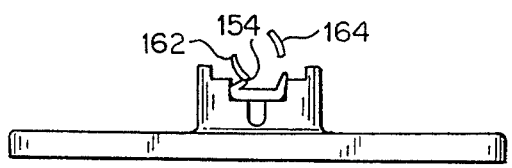
Figure 11E:
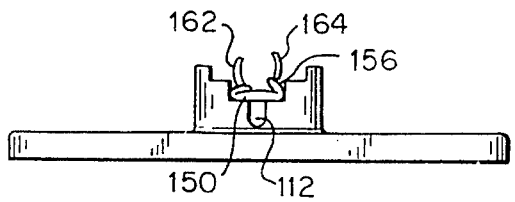
Figure 11F:
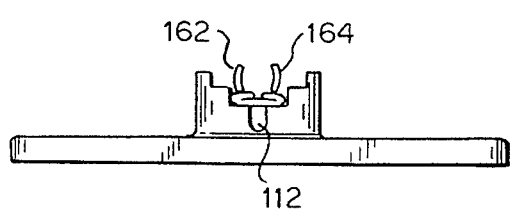

As is seen in FIG. 11c, once the optical portion 150 rests on the platform 114, the blades 162 and 164 are withdrawn upwardly in the direction of arrow 176. Then, as seen in FIG. 11d, the blade 162 engages the haptic portion 154 and begins folding the haptic portion 154 over the optical portion 150 to the position of FIG. 11e. Thereafter, the blade 164 engages the haptic portion 156 and bends the haptic portion 156 over the optical portion 150 until both haptic portions are folded over the optical portion as is shown in FIG. 11f.

Figure 11G:
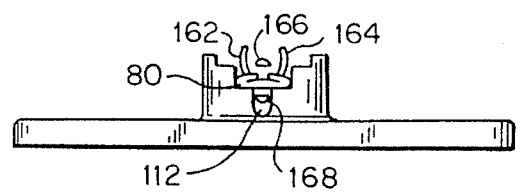

As is seen in FIG. 11g, the blades 166 and 168 of the first holding forceps 170 of FIG. 13 are slid through the slot 104 between the blades 162 and 164 of the first forceps 160 in a direction perpendicular thereto. The instrument groove 112 beneath the lens 80 allows the blade 168 to slide beneath the lens 80 while the blade 166 overlies the lens.

Figure 11H:
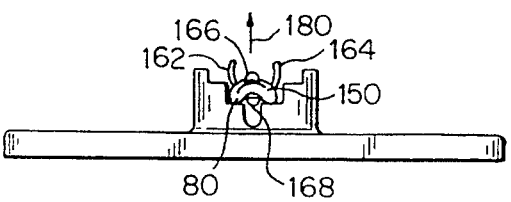

As is seen in FIG. 11*h*, the second holding forceps 170 is then lifted in the direction of arrow 180 so that the blades 168 and 166 move the optical portion 150 of the lens up between the blades 162 and 164 of the first folding forceps 160 which are held in place. This causes lens 80 to bend in half. Since the lens 80 is flexible, bending is accomplished with relative ease.

Figure 11I:
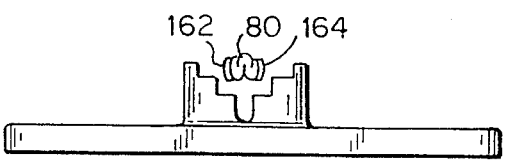

Referring now to FIG. 11*i*, once the lens 80 is completely between the blades 162 and 164 of the first folding forceps 160, the blades 166 and 168 of the second holding forceps 170 are withdrawn and the blades 162 and 164 of the first forceps 160 are squeezed.

As is seen in FIG. 11*i*, the lens 80 is now folded in a w-shape and has a minimal cross-sectional area of less than 3 mm. Accordingly, the lens 80 can be inserted through the surgical incision 78 (see FIG. 4) which is of minimal length, on the order of 3 mm or perhaps less. Since the lens 80 has an elastic memory, once it is released by the blades 162 and 164, it will expand to the substantially planar configurations shown in FIG. 5.

FIGS. 14–17—A Second Embodiment of the Template

Referring now specifically to FIGS. 14–17, a second embodiment of the template, designated generally by the numeral 200 is shown wherein a base 202 has a folding anvil 204 mounted thereon. Folding anvil 204 is in the form of a circular segment and has upper surface 206 with a concave indentation 208 therein. The concave indentation 208 is circular and corresponds to the optical portion 210 of flexible intraocular lens 212 which has a pair of J-style or C-style haptics 214 and 215 extending from an upper surface thereof.

Figure 18A:
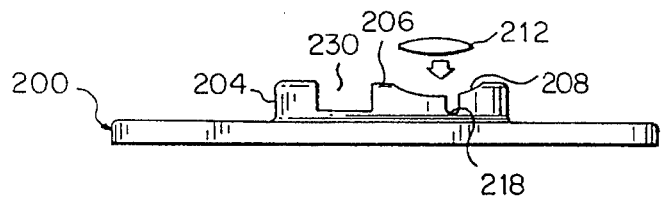
FIGS. 18a–18h are side cross-sectional views of the template of FIGS. 14–17, showing how the template is used in practicing the second method of the instant invention.
Figure 18B:
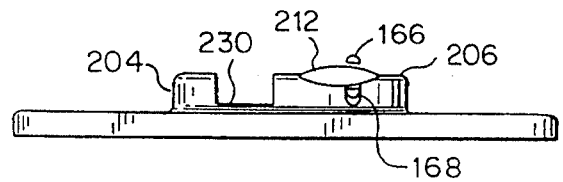

Underlying the circular indentation 208 is a instrument groove 218 which is aligned with a cord 220 of the circle forming the convex indentation 208 rather than a diameter thereof. As is seen in FIG. 18*b*, the groove 218 receives one blade of a forceps, such as the second holding forceps 170 shown in FIG. 13 to initially grip the flexible intraocular lens 212. The J-style or C-style haptics 214 and 215 rest on the top surface of the platform 206.

Disposed laterally of the instrument groove 218 is a second groove 230 which extends parallel to the instrument groove. The second groove 230 is substantially wider and deeper than the instrument groove 218 and as seen in FIGS. 18*c*–18*h*, receives the blades 162 and 164 of the first folding forceps 160 which squeeze the folded lens into an S-shape of minimal dimension.

Figure 18C:
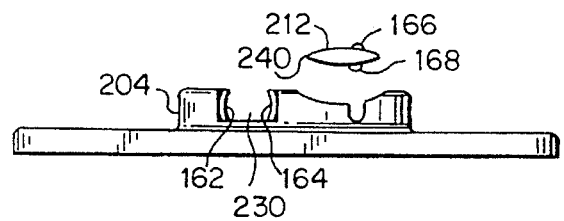
Figure 18D:
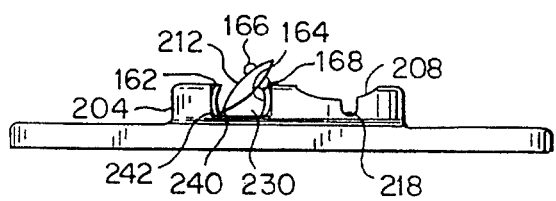

Referring now to FIGS. 18*c*–18*h*, the steps for folding lens 212 are shown in sequence. As is seen in FIG. 18*a* the lens 212 is rested in the concave indentation 208 over the instrument groove 218. The instrument groove 218 is aligned along a cord rather than the diameter of the circular indentation 208 so that when the blades 166 and 168 of the forceps 170 grip the lens, as is seen in FIGS. 18*b* and 18*c*, the lens is gripped along a cord. As is seen in FIG. 18*c*, the blades 162 and 164 of the first folding forceps 160 are positioned in the slot 230, and as seen in FIG. 18*d*, the lens 212 is transferred to a position between the blades 162 and 164. In FIG. 18*d*, the lens 212 is abutted at one edge 240 against bottom edge 242 of blade 162 with the blades 166 and 168 holding the lens in a rotated position.

Figure 18E:
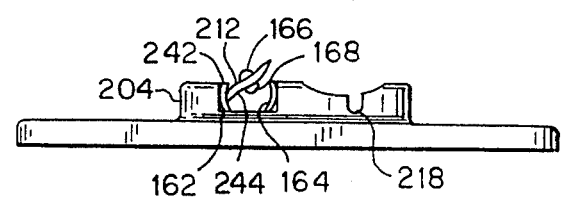
Figure 18F:
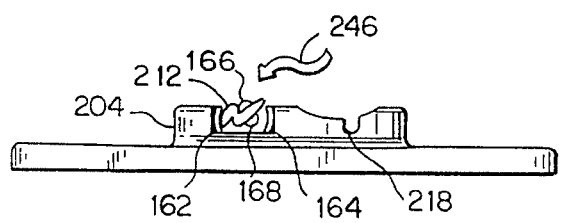
Figure 18G:
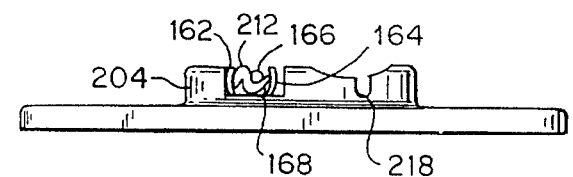
Figure 18H:
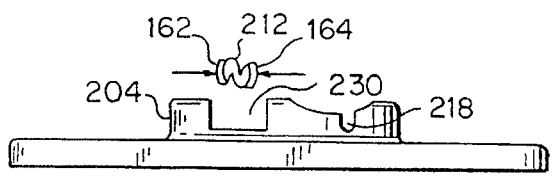
Figure 19:
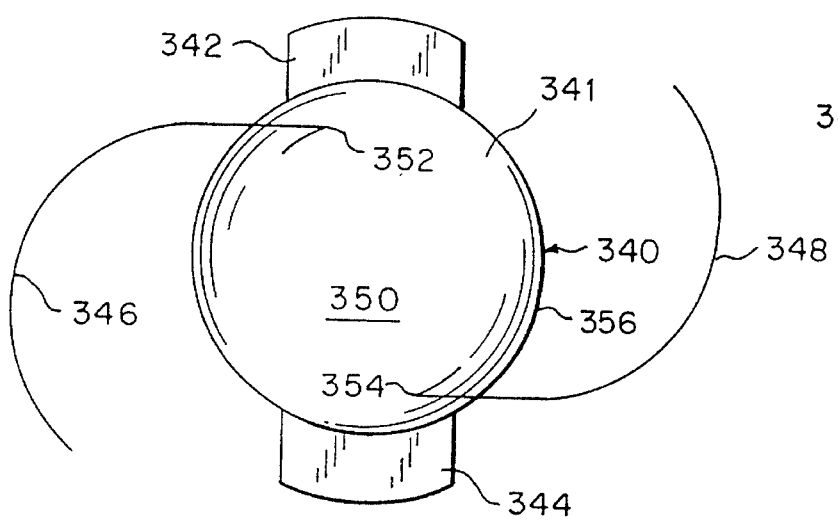
FIG. 19 is a top view of a new and improved flexible, intraocular lens configured in accordance with the principles of the instant invention for use with the method and apparatus of the instant invention as embodied in the template of FIGS. 6–11.
Figure 20:
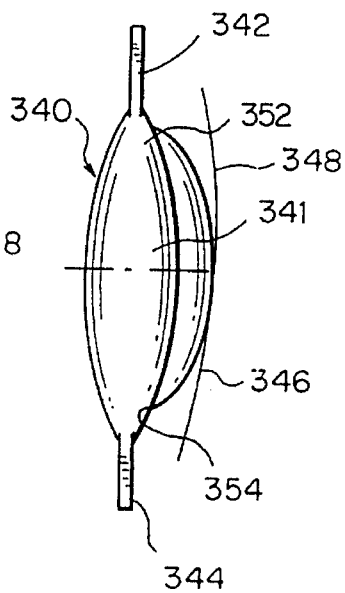
FIG. 20 is a side view of the flexible intraocular lens of FIG. 19.
Figure 21:
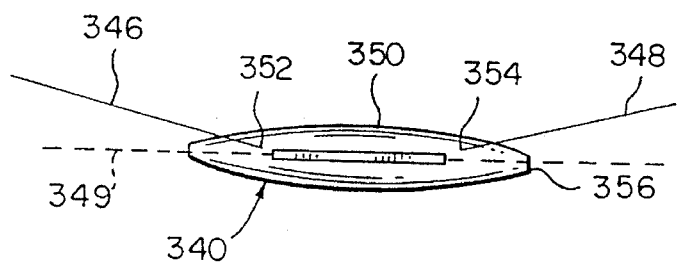
FIG. 21 is an end view of the flexible intraocular lens of FIGS. 19, 20 and 21.
Figure 22:
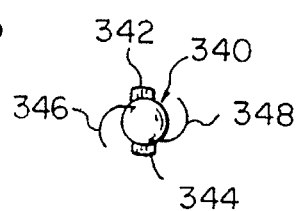
FIG. 22 is a top view of the new and improved lens of FIGS. 20–21 shown in actual size.

As is seen in FIG. 18*e*, the lens 212 is then bent to begin forming first and second folds 242 and 244 by pushing the lens against the blade 162 of the folding forceps 160. As is seen in FIG. 18*f*, the lens is formed into a general S-shape by pressing the blades 166 and 168 of the second holding forceps 170 down between the blades 162 and 164 of the first folding forceps 160 while rotating the second holding forceps slightly in the clockwise direction so that the first holding forceps generally follows the direction of arrow 246. After the lens 212 has been inserted between the blades 162 and 164 of the first folding forceps 160, the lens 212 is completely contained within the forceps 162 and 164 and blades 166 and 168 of the second holding forceps 170 are withdrawn. As is seen in FIG. 18*h*, the blades 162 and 164 are then squeezed together to tightly fold the lens 212 into an S configuration. Again, the lens 212 has a lateral dimension of less than 3 mm and can be inserted through a surgical incision 78 (see FIG. 4) which is of minimal length, on the order of 3 mm or perhaps less. Since the lens 212 has an elastic memory, once it is released by the blades 162 and 164 of the forceps 160, the lens expands to the substantially planner configuration shown in FIG. 4.

FIGS. 19–22: Novel Flexible Intraocular Lens Configuration

Referring now to FIGS. 19–22, there is shown a new and improved flexible intraocular lens, designated generally by the numeral 340. As with the lens 80, the lens 340 includes an optic portion 341 and a pair of plate haptics 342 and 344. In addition, the lens 340, like the lens 212, includes a pair of C-loop and J-loop haptic strands 346 and 348 which cooperate with the structure of the eye for intraocular fixation. As is apparent from FIGS. 19 and 21, the haptic strands 346 and 348 are not coplanar with the lens 340 but extend from one surface 350 of the lens, at points 352 and 354 inboard of the periphery 356 at an acute angle of about 20° with respect to centered plane 349 of the lens. The haptic flanges 342 and 344 assist in the accordion style double folding of the lens 340 while the C- or J-style loops 346 and 348 cooperate with eye structure to fix the lens 340 intraocularly.

From the foregoing description, one skilled in the art can easily ascertain the essential characteristics of this invention and, without departing from the spirit and scope thereof, can made various changes and modifications of the invention to adapt it to various usages and conditions.

I claim:

1. An apparatus specifically configured and dimensioned for folding a specific flexible intraocular lens of preselected dimensions having first and second faces, an optical portion of a selected diameter for alignment with the pupil of an eye, and a pair of opposed plate haptics for attachment to the iris of the eye, the apparatus comprising:

a substantially rigid anvil having an axis of orientation;

a slot through the anvil, the slot extending in the direction of the axis of orientation and having a width at least as wide as the diameter of a lens to be folded;

a stationary platform defined by an indentation in the anvil, the stationary platform being bisected by the slot to form stationary platform halves laterally displaced from one another for supporting the lens to be folded by engaging the plate haptics thereof, each platform half having a shape for corresponding to the shape of one of the pair of opposed plate haptics of the lens being folded;

a stationary land disposed in the slot of the anvil at a location below the stationary platform, the stationary land having a diameter at a location substantially aligned with the slot for engaging substantially only the optical portion of the lens being folded; and a groove in the stationary land aligned with the axis of the slot, whereby the lens being folded in folded twice with first and second forceps having forks by (1) initially mounting the lens on the stationary platform with the plate haptics resting on the stationary platform halves, (2) bending the plate haptics to extend transverse with respect to the optical portion of the lens by displacing the lens to rest on the stationary land, (3) folding the plate haptics to overly the first face of the lens with the forks of the first forceps, (4) gripping the lens by engaging the first and second faces of the lens with the forks of second forceps while holding the plate haptics folded over the first face of the lens with the forks of the first forceps, and (5) folding the lens into a W-shape by lifting the lens from the stationary land with the second forceps to pass between the forks of the first forceps.

2. The apparatus of claim 1, wherein the stationary platform halves are connected to the stationary land by transverse walls which extend transverse to both the stationary platform halves and stationary land, the transverse walls adapted to engage and bend the plate haptics of the lens being folded with respect to the optical portion of the lens being folded when the lens being folded is displaced from the stationary platform halves to the stationary land.

3. The apparatus of claim 2, wherein the transverse walls are substantially parallel proximate the stationary platform halves and wherein the transverse walls diverge from one another at opposite ends of the slot.

4. The apparatus of claim 3, wherein the anvil is mounted on a base having an area substantially larger than the area of the anvil.

5. A template configured and dimensioned for folding a particular type of flexible intraocular lens with first and second two prong forks, the intraocular lens to be folded being of preselected dimensions and having an optical portion of a selected diameter, two faces and plate haptics extending from the optical portion to define the total length of the intraocular lens, the template comprising:

an axis of orientation extending through the template;

a first stationary surface having portions fixed with respect to one another for supporting a lens, the first stationary surface being bisected by a slot with fixed walls having a width less than that of the first stationary surface for receiving unfolded the optical portion of the lens;

orienting surfaces positioned proximate the first stationary surface and defining a shape which is sized and configured for corresponding to the shape of the plate haptics to orient the lens to be folded with the plate haptics extending in a direction perpendicular to the axis of orientation of the template, the orienting surfaces being fixed with respect to one another so as not to move with respect to one another;

a second stationary surface fixed with respect to the first stationary surface and indented from the first stationary surface to form the bottom of the slot, the second surface having portions fixed with respect to one another and being sized and configured for engaging only the optical portion of the lens to be folded, the second surface providing a groove for facilitating insertion of one prong of the second fork in a direction in alignment with the axis of orientation, whereby the template facilitates folding of the lens twice into a W-shaped configuration by 1) initially supporting and orienting the lens on the first stationary surface, 2) supporting the lens on the second stationary surface while the prongs of the first fork hold the plate haptics over a first face of the lens portion and 3) folding the lens portion in half by gripping the lens portion between the prongs of the second fork and moving the lens portion between the prongs of the first fork while the first fork holds the plate haptics folded over the first face of the lens portion.

6. The template of claim 5, wherein the groove in the second surface is coextensive with the axis of orientation.

* * * * *